US006630322B1

(12) United States Patent
Perricaudet et al.

(10) Patent No.: US 6,630,322 B1
(45) Date of Patent: Oct. 7, 2003

(54) GENERATING REPLICATING MOLECULES IN VIVO

(76) Inventors: Michel Perricaudet, 31 rue de Chartres, 28320 Ecrosnes (FR); Patrice Yeh, 11 Bis rue Lacépéde, 75005 Paris (FR); Hélène Leblois-Prehaud, 1 rue Ernest Lavisse, 782280 Guyancourt (FR)

( * ) Notice: Subject to any disclaimer, the term of this patent is extended or adjusted under 35 U.S.C. 154(b) by 0 days.

(21) Appl. No.: 09/194,960

(22) PCT Filed: May 23, 1997

(86) PCT No.: PCT/FR97/00914

§ 371 (c)(1), (2), (4) Date: Dec. 7, 1998

(87) PCT Pub. No.: WO97/47757

PCT Pub. Date: Dec. 18, 1997

(30) Foreign Application Priority Data

Jun. 12, 1996 (FR) ........................................... 96 07273

(51) Int. Cl.$^7$ ......................... C12P 21/06; C12N 15/00; C12N 15/63

(52) U.S. Cl. .................. 435/69.1; 435/91.4; 435/320.1; 435/325; 435/455

(58) Field of Search ...................... 536/23.1; 435/320.1, 435/325, 328, 69.1, 455, 91.4; 514/44; 424/93.6

(56) References Cited

U.S. PATENT DOCUMENTS

| | | | | | |
|---|---|---|---|---|---|
| 5,801,030 | A | * | 9/1998 | McVey et al. | 435/172.3 |
| 6,040,430 | A | * | 3/2000 | Stewart | 530/358 |
| 6,060,273 | A | * | 5/2000 | Dirks et al. | 435/69.1 |
| 6,120,764 | A | * | 9/2000 | Graham et al. | 424/93.6 |
| 6,156,497 | A | * | 9/2000 | Kaleko et al. | 435/5 |
| 6,136,779 | A | * | 10/2000 | Foulkes et al. | 514/1 |

FOREIGN PATENT DOCUMENTS

| | | |
|---|---|---|
| EP | 704 534 | 4/1996 |
| WO | WO 94/29438 | 12/1994 |

OTHER PUBLICATIONS

Eck et al., "Gene–based therapy." Goodman & Gilmans's The Pharmacological Basis of Therapeutics—Ninth Edition, McGraw–Hill: 77–101, 1996.*

Crystal R., "Transfer of genes to human: Early lessons and obstacles to success." Science, vol. 270: 404–410, 1995.*

Verma et al., "Gene therapy—promises, problems and prospects." Nature, vol. 389: 239–242, Sep. 1997.*

Denoarain M., "Ligand–targeted receptor–mediated vectors for gene delivery." Exp. Opin. Ther. Patents, vol. 8(1): 53–69, 1998.*

Miller et al., "Targeted vectors for gene therapy." FASEB, vol. 9:190–199, Feb. 1995.*

Orkin et al. Report & Recommendations of the Panel to Assess the NIH Investment in Research on Gene Therapy 1–20, Dec. 1995.*

Logie et al., Ligand–regulated site–specific recombination, Proc. Natl. Acad. Sci. USA 92(13), 5940–5944 (1995).

Wang et al., High Frequency Recombination Between loxP Sites in Human Chromosomes Mediated by an Adenovirus Vector Expressing Cre Recombinase, Somatic Cell & Molecular Genetics 21(6), 429–441 (1995).

Sakai et al., Efficient Regulation of Gene Expression by Adenovirus Vector–Mediated Delivery of the Cre Recombinase, Biochemical & Biophysical Research Comm. 217(2), 393–401 (1995).

Bergemann et al., Excision of specific DNA–sequences from integrated retroviral vectors via site–specific recombination, Nucleic Acids Research 23(21), 4451–4456 (1995).

Wang et al., Targeted DNA recombination in vivo using an adenovirus carrying the cre recombinase gene, Proc. Natl. Acad. Sci. USA 93, 3932–3936 (1996).

* cited by examiner

*Primary Examiner*—Dave T. Nguyen
(74) *Attorney, Agent, or Firm*—Finnegan, Henderson, Farabow, Garrett & Dunner, L.L.P.

(57) ABSTRACT

The invention discloses circular and replicating DNA molecules, useful in gene therapy, as well as a particularly efficient method for generating them in situ from a viral vector.

20 Claims, 7 Drawing Sheets

Figure 1:
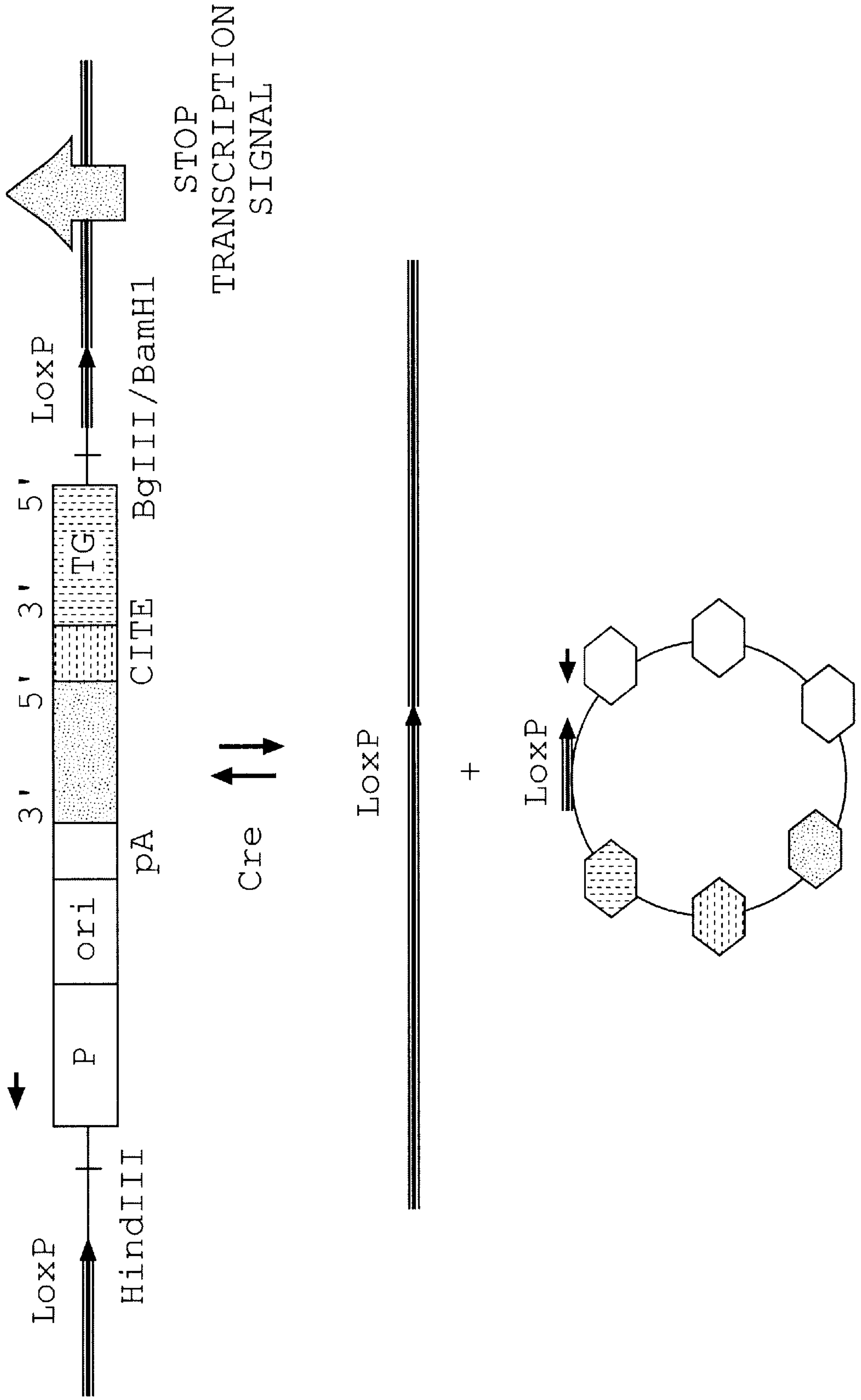

```
CAGCTGGACGTCGG TTCGAA CCGACCTGCATTTGAGGAGAAGTCTGGAT TATTGAAGCATATCGTATG
GTCGACCTGCAGCC AAGCTT GGCTGGACGTAAACTCCTCTTCAGACCTA ATAACTTCGTATAGCATAC
SalI           HindIII                                         LoxP

TAATATGCTTCAATA TAATTCCCAAGGCCTAGTAGCGCTCGAGCTCTAGATCTATAGCTAAC
ATTATACGAAGTTAT ATTAAGGGTTCCGGATCATCGCGAGCTCGAGATCTAGATATCGATTG
                             BamH1/BglII                  claI

GGCGGTGG TAC CGAAGC
CCGCCACC ATG GCTTCG
```

FIG. 3

SEQUENCE LISTING

```
<160> NUMBER OF SEQ ID NOS:  3

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:PCR Primer

<400> SEQUENCE: 1

ggcctctaga cagctggtta ttttcc                                          26


<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 2

ggccggatcc catattatca tcg                                             23


<210> SEQ ID NO 3
<211> LENGTH: 147
<212> TYPE: DNA
<213> ORGANISM: Artificial Sequence
<220> FEATURE:
<223> OTHER INFORMATION: Description of Artificial Sequence: Recombinant
      EBNA-1 replication dependent sequence

<400> SEQUENCE: 3

cagctggacg tcggttcgaa ccgacctgca tttgaggaga agtctggatt attgaagcat     60

atcgtatgta atatgcttca atataattcc caaggcctag tagcgctcga gctctagatc    120

tatagctaac ggcggtggta ccgaagc                                        147
```

GENERATING REPLICATING MOLECULES IN VIVO

This application is filed under 35 U.S.C. §371 of International Application No. PCT/FR97/00914, Filed Jun. 23, 1997.

The present invention relates to circular and replicative DNA molecules which can be used in gene therapy. The invention also describes a particularly efficient method for their generation in situ from a corresponding viral vector.

Gene therapy consists in correcting a deficiency or an abnormality (mutation, aberrant expression and the like) by the introduction of genetic information into the affected organ or cell.

This genetic information may be introduced either in vitro into a cell extracted from the organ, the modified cell then being reintroduced into the body, or directly in vivo into the appropriate tissue. In this second case, various techniques exist, among which are different transfection techniques involving vectors of different types. They may be naturally occurring or synthetic chemical and/or biochemical vectors, on the one hand, or viral vectors on the other. As examples of viral vectors, there may be mentioned especially the complexes of DNA and DEAE-dextran (Pagano et al., J.Virol. 1 (1967) 891), of DNA and nuclear proteins (Kaneda et al., Science 243 (1989) 375), of DNA and lipids (Felgner et al., PNAS 84 (1987) 7413), liposomes (Fraley et al., J.Biol.Chem. 255 (1980) 10431) and the like. However, their use involves especially the possibility of producing large quantities of DNA of pharmacological purity.

Viral vectors (retroviruses, adenoviruses, adeno-associated viruses and the like) are very efficient compared to the chemical and/or biochemical vectors previously described, especially for crossing the membranes. Among these viruses, the adenoviruses exhibit most particularly advantageous properties for use in gene therapy. In particular, they have a fairly broad host spectrum, are capable of transducing dividing cells or quiescent cells and the adenovirus genome persists in extrachromosomal form; furthermore, they have so far not been associated with major pathologies in man. On the other hand, the use of retroviruses whose genome randomly integrates into the genome of the infected cell is limited to dividing cells. The adenoviruses have thus been used to transfer genes of interest into quiescent muscle (myotubes; Ragot et al., Nature 361 (1993) 647)), hepatic (Jaffe et al., Nature genetics 1 (1992) 372), nerve (Akli et al., Nature genetics 3 (1993) 224) and epithelial bronchial (Rosenfeld et al., 1992) cells and the like. However, in rapidly renewable cells, a gradual loss of expression of the transgene by a dilution effect during cell divisions is observed.

The improvement of adenoviral vectors and the development of new generations of vectors have been aimed at reducing the residual potential risks of pathogenicity as well as the potential risks of immunogenicity linked to the replication of the vector, the recombination of its genome and the expression of viral proteins.

To avoid such risks as much as possible, the viral vector constructs currently proposed are modified so as to make the said vectors incapable of autonomously replicating in the target cell. They are said to be defective. Generally, the genome of the defective viruses therefore lacks at least sequences necessary for the replication of the said virus in the infected cell. Thus, in the specific case of adenoviruses, the constructs described in the prior art are adenoviruses deleted of E1 and optionally E3 regions at the level of which the heterologous DNA sequences are inserted (Levrero et al., Gene 101 (1991) 195; Gosh-Choudhury et al., Gene 50 (1986) 161). Other constructs comprise a deletion at the level of the E1 region and of a non-essential part of the E4 region (WO94/12649), or a modified genomic organization (FR 94 13355).

However, the risk of recombinations generating replicative viral particles or transcomplementations in vivo by E1-type cellular functions remains during the production of these defective viral vectors. It is clear that the use in gene therapy of vectors thus contaminated may have very damaging consequences such as, for example, inducing a viral propagation and causing an uncontrolled dissemination with risks of an inflammatory reaction and of an immune response directed against the viral proteins, and the like.

Moreover, the enhancement of the stability of the expression of the transgene in the transduced cells by the adenoviral vector, and more particularly in dividing cells, remains a major problem to be solved. Consequently, a real need for transfer vectors which would essentially manifest the advantages of each of the vectors described above, namely good transfection properties based, for example, on those of the viral vectors and in particular those of the adenoviruses and a perfect safety resulting in particular in an absence of generation of replicative viral particles in vivo, a risk which is inexistant with plasmids or non-viral vectors, remains up until now in gene therapy.

The object of the present invention is precisely to propose a new concept of gene transfer which meets the abovementioned requirements.

The present invention consists especially in the in situ generation, via a viral vector, of therapeutic replicative circular DNA molecules which are advantageous from the point of view of the stability of expression of the transgene and of safety. Indeed, they are free of any sequence of the viral genome capable of inducing an inflammatory-type immune response as well as a specific response directed against the viral proteins which may have a deleterious effect on the body and limit the duration of expression of the transgene.

The subject of the present invention is thus replicative circular DNA molecules comprising at least:

(i) one or more genes of interest with the sequences necessary for their expression, (ii) a replication origin functional in mammalian cells, and (iii) a sequence resulting from the site-specific recombination between two sequences recognized by a recombinase.

The present invention stems in particular from the development of a process and of specific constructs which are particularly efficient for the production of these therapeutic DNA molecules. More particularly, the process according to the invention consists in the production of the therapeutic DNA molecules defined above from a viral vector.

Surprisingly, the applicant has thus demonstrated that it is possible to generate in situ, from a viral vector and by site-specific recombination, a circular DNA molecule with a therapeutic and replicative character. Furthermore, in an advantageous embodiment, the transgene and the replication origin are inactive in the viral vector, their activity being dependent on the site-specific recombination event.

Still more advantageously, the recombination event is induced conditionally by the expression of recombinase, thereby offering a high level of control over the expression of the gene of interest and over the replication of the episomal molecules produced.

Such a procedure is particularly advantageous from the therapeutic point of view:

- it takes advantage of the good transfection capacities generally manifested by the viral vectors compared to the non-viral vectors,
- it considerably reduces the risks of viral contamination, of local inflammatory reaction as well as of antiviral immune response, given the small quantity of viral vectors used. The latter is introduced only in a proportion necessary for the generation of the therapeutic DNA molecule,
- it makes it possible to broaden the field of application of some viral vectors: thus, the adenoviral vectors have limited applications in proliferative cells such as haematopoietic stem cells. The present invention makes it possible to exploit their infectivity in order to generate, in proliferative cells, stable replicative circular molecules.

The DNA molecule as claimed therefore has the ability to efficiently ensure the transfer, into the intended cells, of the therapeutic gene(s) which it contains.

To do this, it contains a replication origin characterized especially by the fact that it is functional in mammalian and human cells. Advantageously, the replication origin used is a conditional replication origin, that is to say whose activity may be regulated. Still more preferably, the replication origin is arranged such that it is inactive in the viral vector, and active after the site-specific recombination.

Advantageously, the replication origin used is of eukaryotic, viral or mammalian origin.

A preferred example of a replication origin which may be used within the framework of the present invention is more particularly the Epstein-Barr (EBV) virus replication origin. The EBV virus belongs to the Herpesviridae family. Its replication origin comprises two elements: the oriP sequence (1.7 kb) responsible for the replication, whose activity is induced by the protein encoded by the EBNA1 gene. This sequence may be carried in trans. These elements allow, on their own, at the same time the replication, the episomal maintenance and to the segregation of 5 to 20 copies per cell of a plasmid vector. The oriP sequence is composed of a repetition of 20 units of 30 bp, separated by 960 bp from the replication origin which is formed by an inverted repeat unit of 65 bp and comprises 4 imperfect copies of the 30 bp unit. The EBNA1 protein attaches to the 30 bp units at the level of the replication origin and allows the recruitment of cellular factors at the time of the S phase and the replication, synchronously with cell division, of a plasmid having the oriP sequence in cis. Furthermore, EBNA1, probably through the simultaneous attachment at the level of the repeat units and of chromosomal structures, allows intranuclear maintenance and the segregation of the episome at the time of cell division. Plasmids containing the replication origin oriP of the EBV genome and allowing the expression of the EBNA1 viral protein (641 amino acids) are maintained in a stable episomal manner in the transfected human cells and their replication is synchronous with cell division (Lupton and Levine, 1985).

The replication origin may also be derived from papilloma viruses. Papilloma viruses use a system of viral latency with episomal maintenance of the genome analogous to that of the Epstein-Barr virus (EBV). This system has been particularly studied for the type 1 bovine papilloma virus (BPV-1). The replication origin of BPV is active in the presence of the proteins E1 and E2. As in the case of EBV, the episomal maintenance is independent of replication and is ensured by the attachment of E2 at the level of the MME (minichromosome maintenance element) sequence, but also requires the presence of E1. On the other hand, contrary to the EBV oriP/EBNA1 system, the replication of the episome is not synchronous with cell division (Piirsoo et al., 1996).

The replication origin may also consist of sequences capable of autonomous replication or ARS (autonomously replicating sequences). ARSs have been isolated from chromosomes of mammals, especially man and mice. Preferably, there may be mentioned the ARS sequence localized upstream of the c-myc locus in man (Ariga et al., 1988) and the 4 kb fragment of the locus of the mouse adenosine deaminase gene (Virta-Pearlman et al., 1993).

As regards the gene of interest, it may be a therapeutic, vaccinal, agronomic or veterinary gene. It also contains a transcriptional promoter region functional in the target cell or organism, as well as a region situated in 3' and which specifies a signal for termination of transcription and of polyadenylation. As regards the promoter region, it may be a promoter region naturally responsible for the expression of the gene considered when the said promoter region is capable of functioning in the relevant cell or organism. It may also be regions of different origin (responsible for the expression of other proteins, or even synthetic). In particular, this may be promoter sequences of eukaryotic or viral genes. For example, this may be promoter sequences derived from the genome of the target cell. Among the eukaryotic promoters, there may be used any promoter or derived sequence stimulating or repressing the transcription of a gene specifically or otherwise, inducibly or otherwise, strongly or weakly. They may be in particular ubiquitous promoters (promoters of the HPRT, PGK, α-actin and tubulin genes and the like), promoters of the intermediate filaments (promoters of the GFAP, desmin, vimentin, neurofilament and keratin genes and the like), promoters of therapeutic genes (for example the promoter of MDR, CFTR, factor VIII and ApoAI genes and the like), tissue-specific promoters (promoter of the pyruvate kinase, villin, fatty acid-binding intestinal protein and smooth muscle alpha-actin gene and the like) or alternatively promoters responding to a stimulus (receptor for the steroid hormones, retinoic acid receptor and the like). Likewise, they may be promoter sequences derived from the genome of a virus, such as for example the promoters of the adenovirus E1A and MLP genes, the early CMV promoter or alternatively the promoter of the RSV LTR, and the like. In addition, these promoter regions may be modified by addition of activating sequences, regulatory sequences or sequences allowing a tissue-specific or predominant expression. Moreover, the gene of interest may also comprise a signal sequence directing the product synthesized in the secretory pathways of the target cell. This signal sequence may be the natural signal sequence of the product synthesized, but it may also be any other functional signal sequence or an artificial signal sequence.

A promoter of viral origin chosen from the early CMV promoter or the LTR of a retrovirus or a mammalian promoter is advantageously used.

In addition to a replication origin and at least one gene of interest, the DNA molecules of the invention comprise a region resulting from the specific recombination between two sequences. This site-specific recombination may be obtained from various systems which bring about site-specific recombination between sequences.

The specific recombination system used within the framework of the present invention for the in situ generation of the claimed DNA molecules may be of various origins. In particular, the specific sequences and the recombinases used may belong to different structural classes, and especially to the bacteriophage P1 recombinase family.

More preferably, the site-specific recombination used according to the process of the invention is obtained by means of two specific sequences which are capable of recombining with each other in the presence of a specific protein, generally designated recombinase. It is for this reason that the circular DNA molecules according to the invention comprise, in addition, a sequence resulting from this site-specific recombination. The sequences allowing the recombination used within the framework of the invention generally comprise from 5 to 100 base pairs, and more preferably less than 50 base pairs.

Among the recombinases belonging to the bacteriophage 1 integrase family, there may be mentioned especially the integrase of the phages lambda (Landy et al., Science 197 (1977) 1147), P22 and F80 (Leong et al., J. Biol. Chem. 260 (1985) 4468), HP1 of *Haemophilus influenzae* (Hauser et al., J. Biol. Chem. 267 (1992) 6859), the integrase Cre of the P1 phage, the integrase of the pSAM2 plasmid (EP 350 341) or alternatively the FLP recombinase of the plasmid 2 m of the yeast Saccharomyces cerevisiae. When the DNA molecules according to the invention are prepared by recombination by means of a site-specific system of the lambda bacteriophage integrase family, the DNA molecules according to the invention generally comprise, in addition, a sequence resulting from the recombination between two sequences for attachment att of the corresponding bacteriophage or plasmid.

Among the recombinases belonging to the transposon Tn3 family, there may be mentioned especially the resolvase of the transposon Tn3 or of the transposons gd, Tn21 and Tn522 (Stark et al., 1992); the invertase Gin of the bacteriophaqe mu or alternatively the resolvase of plasmids, such as that of the fragment par of RP4 (Abert et al., Mol. Microbiol. 12 (1994) 131). When the DNA molecules according to the invention are prepared by recombination by means of a site-specific system of the transposon Tn3 family, the DNA molecules according to the invention generally comprise, in addition, a sequence-resulting from the recombination between two sequences for recognition of the resolvase of the transposon considered.

According to a preferred embodiment, in the genetic constructs of the present invention, the sequences allowing the site-specific recombination are derived from a bacteriophage. More preferably, they are sequences for attachment (attp and attB sequences) of a bacteriophage or of derived sequences. These sequences are capable of specifically recombining with each other in the presence of a recombinase designated integrase. The term derived sequence includes the sequences obtained by modification(s) of the sequences for attachment of bacteriophages, which retain the capacity to recombine specifically in the presence of the appropriate recombinase. Thus they may be reduced fragments of these sequences or on the contrary fragments extended by addition of other sequences (restriction sites and the like). They may also be variants obtained by mutation(s), especially by point mutation(s). According to the invention, attP and attB sequences of a bacteriophage or of a plasmid designate the sequences of the recombination system specific to the said bacteriophage or plasmid, that is to say the attP sequence present in the said phage or plasmid and the corresponding chromosomal attB sequence.

By way of preferred examples, there may be mentioned especially the sequences for attachment of the lambda phages P22, F80, P1, HP1 of *Haemophilus influenzae* or alternatively of the plasmid pSAM2, or 2 m.

According to a preferred embodiment of the invention, the sequences allowing the site-specific recombination are derived from the recombination system of the P1 phage. This P1 phage possesses a recombinase called Cre which specifically recognizes a 34-base pair nucleotide sequence called lox P site. This sequence is composed of two palindromic sequences of 13 bp separated by a conserved sequence of 8 bp.

In a specific variant, the invention therefore relates to a circular and replicative DNA molecule comprising (a) a sequence derived from the site-specific recombination between two loxP regions of the P1 bacteriophage, at least one gene of interest and one replication origin functional in mammalian and human cells and which, according to a preferred mode, possesses a conditional functionality.

In this regard, the present invention also provides specific gene constructs appropriate for the production of the therapeutic DNA molecules defined above. These gene constructs, or recombinant DNAs according to the invention comprise especially the gene(s) of interest, the replication origin and the EBNA1 protein gene surrounded by the two sequences allowing the site-specific recombination positioned in direct orientation. These sequences may be cloned in the form-of cassettes into bacterial plasmids, it being possible for the plasmid DNA, in the first instance, to be transfected into human cells in order to test the functionality of these sequences. These cassettes are then used to construct viral vectors possessing these same sequences integrated into their genome.

As indicated above, another aspect of the present invention consists in a process for the in situ production of therapeutic DNA molecules defined above from a viral vector by site-specific recombination. The use of such a vector makes it possible advantageously to optimize the administration of the DNA molecule claimed in the cells to be treated.

In this regard, the subject of the present invention is also a viral vector comprising, inserted into its genome, at least one DNA region surrounded by two sequences allowing a site-specific recombination and positioned in direct orientation, the said DNA region comprising at least one replication origin and one gene of interest.

According to a preferred embodiment of the invention, the replication origin as well as the gene of interest which are integrated into the viral vector are present in an inactivated form, the promoter being cloned in direct orientation at one of the ends of the expression cassette (FIG. 1). After recombination between the two LoxP sites, the promoter finds itself in front of the gene of interest and separated therefrom by a LoxP site, the first ATG of the transcript corresponding to the codon for initiation of the transgene. The orip sequence is active only in the presence of the EBNA1 protein, the latter is expressed under the control of the same promoter as the transgene, in the form of a bicistronic messenger. The translation of EBNA1 is initiated by a mechanism of internal initiation at the level of an IRES sequence derived from the encephalomyocarditis virus (ECMV), of the picornavirus family. The expression of the transgene and of the EBNA1 protein as well as the replication of the plasmid are therefore directly determined by the recombination event between the two LoxP sites.

According to another variant of the invention, the encapsidation region of the virus is included in the replicon (the DNA region surrounded by the sequences allowing the site-specific recombination). This embodiment offers an additional safety to the system, as explained later.

The viral vector used may be of various origins, as long as it is capable of transducing animal cells and preferably human cells. In a preferred embodiment of the invention, vectors derived from adenoviruses, adeno-associated viruses (AAV), herpes viruses (HSV) or retroviruses are used. It is most particularly advantageous to use an adenovirus for a direct administration or for the modification ex vivo of cells-intended to be implanted, or a retrovirus, for the implantation of producing cells.

The viruses according to the invention are defective, that is to say they are incapable of autonomously replicating in the target cell. Generally, the genome of the defective viruses used within the framework of the present invention therefore lacks at least sequences necessary for the replication of the said virus in the infected cell. These regions may be either eliminated (completely or partly), or made non-functional, or substituted by other sequences and especially by the heterologous nucleic sequence of interest. Preferably, the defective virus retains, nevertheless, the sequences of its genome which are necessary for the encapsidation of the viral particles.

As regards more particularly adenoviruses, the type 2 or 5 human adenoviruses (Ad2 or Ad5) or adenoviruses of animal origin (see application WO94/26914) are preferably used within the framework of the present invention. Among the adenoviruses of animal origin which may be used within the framework of the present invention, there may be mentioned the adenoviruses of canine, bovine, murine (example: Mav1, Beard et al., Virology 75 (1990) 81), ovine, porcine, avian or alternatively simian (example: SAV) origin.

Preferably, the viral vectors of the invention are defective adenoviruses comprising, inserted into their genome, a gene sequence comprising at least-one replication origin and one gene of interest and surrounded by two sequences positioned in direct orientation. These make it possible to induce a conditional activity of the replication origin and of the transgene, by means of the site-specific recombination, dependent on the presence of recombinase.

Advantageously, in the genome of these adenoviruses of the invention, at least the E1 region is made non-functional. Still more preferably, the E1 gene and at least one of the E2, E4, L1–L5 genes are non-functional. Other regions may also be modified, and especially the E3 (WO90/02697), E2 (WO94/28938), E4 (WO94/28152, WO94/12649, WO95/02697) and L5 (WO95/02697) region.

According to a preferred embodiment, the adenovirus according to the invention comprises a deletion in the E1 and E4 regions and the DNA region surrounded by the two sequences allowing a site-specific recombination is inserted at the level of the inactivated E1 region. According to another preferred embodiment, it comprises a deletion in the E1 and E4 regions and the DNA region surrounded by the two sequences allowing a site-specific recombination is inserted at the level of the inactivated E4 region. As indicated below, according to a specific embodiment of the invention, the adenovirus also comprises a cassette for expression of the recombinase gene.

The claimed vectors are obtained by recombination with plasmids as defined above, that is to say characterized by the fact that they comprise, between two site-specific recombination regions, at least one replication origin and one gene of interest with conditional activity.

As regards more particularly the definitions of replication origin, of the two sequences allowing a site-specific recombination and of the gene of interest which are present in the DNA region integrated into the claimed viral vector, reference will be made to the abovementioned definitions.

The defective recombinant adenoviruses according to the invention may be prepared by any technique known to persons skilled in the art (Levrero et al., Gene 101 (1991) 195, EP 185 573; Graham, EMBO J. 3 (1984) 2917). In particular, they may be prepared by homologous recombination between an adenovirus and a plasmid carrying, inter alia, the DNA sequences of the invention, or by construction of a viral genome in *E. coli*. The homologous recombination occurs after cotransfection of the said adenovirus and plasmid into an appropriate cell line. The cell line used should preferably (i) be transformable by the said elements, and (ii) comprise the sequences capable of complementing the defective adenovirus genome part, preferably in an integrated form to avoid the risks of recombination. By way of example of a line, there may be mentioned the human embryonic kidney line 293 (Graham et al., J. Gen. Virol. 36 (1977) 59) which contains especially, integrated into its genome, the left part of the genome of an Ad5 adenovirus (12%) or of the lines capable of complementing the E1 and E4 functions as described especially in applications No. WO 94/26914 and WO95/02697.

The adenoviruses which have multiplied are then recovered and purified according to conventional molecular biology techniques as illustrated in the examples.

As regards the adeno-associated viruses (AAV), they are DNA viruses of a relatively small size, which integrate into the genome of the cells which they infect, in a stable and site-specific manner. They are capable of infecting a broad spectrum of cells without inducing any effect on cellular growth, morphology or differentiation. Moreover, they do not appear to be involved in pathologies in man. The AAV genome has been cloned, sequenced and characterized. It comprises about 4700 bases and contains, at each end, an inverted repeat region (ITR) of about 145 bases, serving as replication origin for the virus. The rest of the genome is divided into 2 essential regions carrying the encapsidation functions: the left part of the genome, which contains the rep gene involved in the viral replication and the expression of the viral genes; the right part of the genome, which contains the cap gene encoding-the viral capsid proteins.

The use of AAV-derived vectors for the transfer of genes in vitro and in vivo has been described in the literature (see especially WO 91/18088; WO 93/09239; U.S. Pat. No. 4,797,368, U.S. Pat. No. 5,139,941, EP 488 528). These applications describe various AAV-derived constructs in which the rep and/or cap genes are deleted and replaced by a gene of interest, and their use for transferring in vitro (on cells in culture) or in vivo (directly into an organism) the said gene of interest. The defective recombinant AAVs according to the invention may be prepared by cotransfection, into a cell line infected by a human helper virus (for example an adenovirus), of a plasmid containing the nucleic sequences of the invention bordered by two AAV inverted repeat regions (ITR), and of a plasmid carrying the AAV encapsidation genes (rep and cap genes). The recombinant AAVs produced are then purified by conventional techniques.

As regards the herpes viruses and the retroviruses, the construction of recombinant vectors has been widely described in the literature: see especially Breakfield et al., New Biologist 3 (1991) 203; EP 453242, EP178220, Bernstein et al. Genet. Eng. 7 (1985) 235; McCormick, BioTechnology 3 (1985) 689, and the like.

In particular, the retroviruses are integrative viruses selectively infecting dividing cells. They therefore constitute vectors of interest for cancer applications. The genome of retroviruses comprises essentially two LTRs, an encapsidation sequence and three coding regions (gag, pol and env). In the recombinant vectors derived from retroviruses, the gag, pol and env genes are generally deleted, completely or partly, and replaced with a heterologous nucleic acid sequence of interest. These vectors may be made from various types of retroviruses, such as especially MoMuLV ("murine moloney leukaemia virus", also called MOMLV), MSV ("nmurine moloney sarcoma virus"), HaSV ("harvey sarcoma virus"); SNV ("spleen necrosis virus"); RSV ("Rous sarcoma virus") or alternatively Friend's virus.

To construct recombinant retroviruses according to the invention, a plasmid comprising especially the LTRs, the encapsidation sequence and the sequences of the invention is generally constructed and then used to transfect a so-called encapsidation cell line capable of providing in trans the retroviral functions which are deficient in the plasmid. Generally, the encapsidation lines are therefore capable of expressing the gag, pol and env genes. Such encapsidation lines have been described in the prior art, and especially the PA317 line (U.S. Pat. No. 4,861,719); the PsiCRIP line (WO90/02806) and the GP+envAm-12 line (WO89/07150). Moreover, the recombinant retroviruses may comprise modifications at the level of the LTRs to suppress-the transcriptional activity, as well as extended encapsidation sequences comprising part of the gag gene (Bender et al., J. Virol. 61 (1987) 1639). The recombinant retroviruses produced are then purified by conventional techniques.

By way of preferred vectors according to the invention, there may be proposed more particularly adenoviruses comprising, in their genome, a DNA region in accordance with the invention and bordered by inverted repeat sequences of the P1 bacteriophage (loxP region) positioned in direct orientation.

By way of illustration of this type of vectors, there may be mentioned more particularly the following constructs with the β-galactosidase (LacZ) gene or the thymidine kinase gene of the herpes virus (TK), (FIG. 1). The gene of interest may be any gene (cDNA, gDNA, RNA, synthetic or semi-synthetic nucleic acid) encoding an RNA or a therapeutic or vaccinal protein such as enzymes, blood derivatives, hormones, lymphokines: interleukins, interferons, TNF and the like (FR 9,203,120), growth factors, neurotransmitters or precursers thereof or synthesis enzymes, trophic factors: BDNF, CNTF, NGF, IGF, GMF, αFGF, βFGF, NT3, NT5 and the like; apolipoproteins: ApoAI, ApoAIV, ApoE and the like (FR 93 05125), dystrophin or a minidystrophin (FR 9111947), the tumour suppressor genes: p53, Rb, RaplA, DCCm, k-rev and the like (FR 93 04745), the genes encoding factors involved in coagulation: factors VII, VIII, IX and the like, or alternatively all or part of a natural or artificial immunoglobulin (Fab, ScFv and the like), a ligand RNA (WO91/19813) and the like.

The gene of interest may also be an antisense sequence whose expression in the target cell makes it possible to control the expression of genes or the transcription of cellular mRNAs. Such sequences may be for example transcribed, in the target cell, into RNA complementary to cellular mRNAs and thereby block their translation into protein, according to the technique described in patent EP 140 308.

The vectors of the invention are particularly suited to the expression of sequences encoding toxic factors. These may be in particular poisons for cells (diphtheria toxin, pseudomonas toxin, ricin A and the like), a product inducing sensitivity to an external agent (suicide genes: thymidine kinase, cytosine deaminase and the like) or alternatively killer genes capable of inducing cell death (Grb3-3 (PCT/FR94/00542), anti-ras ScFv (WO94/29446) and the like). The system of the invention indeed makes it possible to produce vectors, especially viral vectors, containing these sequences without toxicity to the producing cells, and then to induce the expression of these toxic molecules selectively in target cells after site-specific recombination. This type of construct is therefore particularly suited to strategies of antitumour therapies, for example, in which the aim is to selectively destroy the affected cells. This system is also particularly advantageous for the expression of cytokines, interferons, TNF or TGF for example, of which an uncontrolled production may have very marked side effects.

The present invention is also aimed at any eukaryotic cell transfected with at least one viral vector or a DNA molecule according to the invention as defined above.

Another object of the present invention consists in a process for the production of a DNA molecule as defined above, according to which a culture of host cells containing a viral vector according to the invention is brought into contact with the recombinase allowing the site-specific recombination to be induced.

More precisely, the present invention relates in general to any preparation process characterized in that it brings into contact:

(i) modified host cells containing at least one viral vector, the said vector comprising in its genome at least one DNA region, surrounded by two sequences allowing a site-specific recombination and positioned in direct orientation, the said region comprising at least one replication origin and one gene of interest and (ii) the recombinase allowing the site-specific-recombination to be induced in situ, for generating the said circular and replicative DNA molecules.

Various procedures may be proposed within the framework of the present invention for bringing the viral vector into contact with the specific recombinase. It may be performed in particular at the level of the host cell either by cotransfection with a plasmid or co-infection with a viral vector containing the gene for the said recombinase, or by induction of the expression of a gene encoding the said recombinase directly present in the genome of the said host cell. The gene encoding the recombinase may therefore be present in the host cell in a form integrated into the genome, on a plasmid or alternatively on an accompanying viral vector of the adenovirus type, for example. In this case, the viral vector used to generate the DNA molecule according to the invention is as defined above.

According to another method, the cassette for expressing the gene is carried on the viral vector which is also responsible for the expression of the gene of interest.

In this particular case, the process according to the invention uses a viral vector comprising in its genome, in addition to a DNA region delimited by two sequences encoding specific recombination sites and comprising at least one replication origin and one gene of interest, a cassette for expressing the recombinase gene.

Such a vector constitutes another object of the present invention.

In this regard, according to a specific variant, the invention relates to an adenovirus comprising a first deletion in the E1 region into which the replicon (the DNA region surrounded by two site-specific recombination sequences) is inserted and a deletion made in E4 and/or E3 at the level of which the cassette for expressing the recombinase protein is inserted.

In contrast to the embodiment described above, the replicon may be inserted into the deleted part corresponding to the E3 or E4 region while the cassette for expressing the recombinase is inserted at the level of the deleted E1 region.

According to another variant, the replicon as well as the cassette for expressing the recombinase are inserted at the level of the defective E1 region.

More particularly, as indicated above, the sequences allowing the site-specific recombination are the LoxP sequences and the recombinase is the Cre protein whose mode of action on the said recombination sequences has been described above.

According to a preferred embodiment of the invention, it would in fact be desirable to be able to control and in particular to induce the expression of this recombinase within the host cell. To this end, it is advantageously proposed, within the framework of the present invention, to control the expression of the gene encoding the recombinase. To do this, it is proposed to place the expression of the said gene under the control of a regulatory element. This may be especially an inducible promoter which makes it possible to control the levels and/or the periods of expression of this gene, such as for example the MMTV LTR promoter (Pharmacia), which is induced by dexamethasone or a promoter regulated by tetracycline (WO94/29442; WO94/04672). It is understood that other promoters may be used, and especially MMTV LTR variants carrying, for example, heterologous regulatory regions (especially "enhancer" regions).

In another embodiment, the expression of the gene encoding the recombinase is under the control of promoters which are regulated so as to avoid either a constitutive accumulation of the said protein in the host cell, or to minimize "leakage" towards the nuclear compartment and a degree of cytotoxicity. Elements which function as transcriptional transactivation domains may thus be associated with them. By way of representatives of this type of elements, there may be mentioned especially the hormone receptors including the steroid, retinoid acid and thyroid receptors among which there may be mentioned more particularly those for the glucocorticoids, mineralocorticoids, thyroids, oestrogen, aldosterone and retinoic acid. This type of construct between the recombinase Cre and the DNA-binding domain of a glucocorticoid receptor has been described for example in Feil et al. (PNAS 93 (1996) 10887).

Figure 6A:
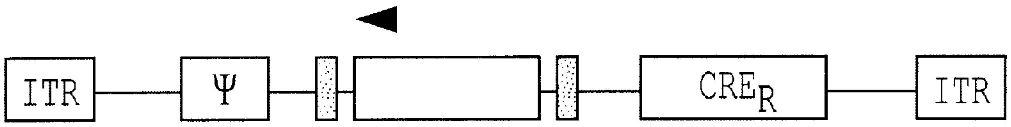
Figure 6B:
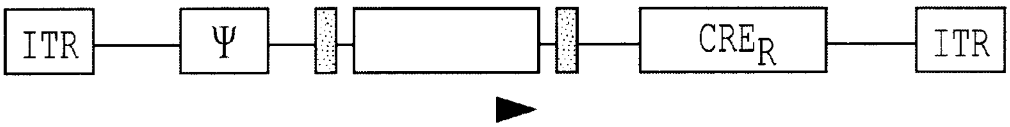
Figure 7A:
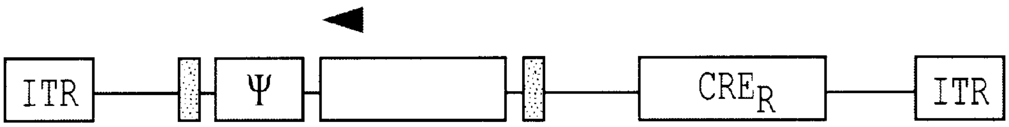
Figure 7B:
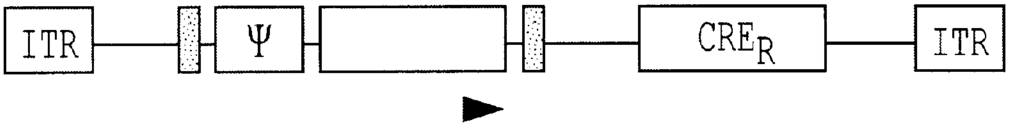

The possibility of regulating the expression of the recombinase is particularly important in the case of the vectors of the invention carrying both the replicon and the recombinase expression cassette. Indeed, in this embodiment, if the recombinase is expressed for example during the production of the viral vectors, the replicon will be excised from the viral genome before its encapsidation. For this reason, it is useful to be able to have a system in which the expression of the recombinase protein is repressed in the virus producing cells. This is obtained as indicated above using a regulated promoter (tetracycline or MMTV type), and/or a hormone receptor type element which, associated with the recombinase, maintains it in the extranuclear compartment in the absence of the said hormone (FIGS. 6 and 7). Because of this, in the absence of the hormone, the recombinase cannot act, and in the presence of the hormone, the latter is then transported to the nuclear compartment where it exerts its activity.

An advantageous approach for controlling the expression of the recombinase consists in using a ecombinase fused with a hormonal receptor (DNA-binding omain), and therefore inactive in the absence of the said hormone, and then in placing the said gene in the viral vector such that it is under the control of the promoter of the replicon. This embodiment is represented for example in FIG. 6*b*.

Moreover, to increase the safety of the system, it is also possible, as indicated above, to include, in the replicon, the region for encapsidation of the viral vector (FIG. 7). This makes it possible to avoid the virus stock produced from becoming contaminated by vectors which have lost their replicon. Indeed, if in spite of the regulatory systems stated above an active recombinase expression occurs during the production of the virus, this will bring about the excision of the replicon from the viral genome and thus the generation of viral genomes free of replicon. If the region for encapsidation of the virus is carried by the said replicon, the viral genomes thus generated will not be encapsidated. Thus, only the viral genomes carrying both the replicon and the recombinase expression cassette can be encapsidated.

The subject of the present invention is also pharmaceutical compositions comprising at least one viral vector according to the invention or a transfected cell according to the invention. These compositions may be formulated for administration by the topical, oral, parenteral, intranasal, intravenous, intramuscular, subcutaneous or intraocular route and the like. Preferably, the composition according to the invention contains pharmaceutically acceptable vehicles for an injectable formulation. They may be in particular isotonic sterile saline solutions (monosodium or disodium phosphate, sodium, potassium, calcium or magnesium chloride and the like, or mixtures of such salts), or dry, especially freeze-dried, compositions which, upon addition depending on the case of sterilized water or of physiological saline, allow the constitution of injectable solutions. As regards the retroviruses, they may be advantageous to use directly the encapsidation cells or cells infected ex vivo for the purpose of their reimplantation in vivo, optionally in the form of neo-organs (WO94/24298).

The doses of vector used for the injection may be adjusted according to various parameters, and especially according to the mode of administration used, the relevant pathology or alternatively the desired duration of the treatment. In general, the recombinant viruses according to the invention are formulated and administered in the form of doses of between $10^4$ and $10^{14}$ pfu/ml. For the AAVs and adenoviruses, doses of $10^6$ to $10^{10}$ pfu/ml may also be used. The term pfu ("plaque forming unit") corresponds to the infectivity of a suspension of virions and is determined by infecting an appropriate cell culture and measuring, generally after 48 hours, the number of plates of infected cells. The techniques for determining the pfu titre of a viral solution are well documented in the literature.

According to the gene of interest present in the DNA molecules of the invention or the regions integrated into the genome of the said viral vectors, these may be used for the treatment or prevention of numerous pathologies including genetic diseases (myodystrophy, cystic fibrosis and the like), neurodegenerative diseases (Alzheimer, Parkinson, ALS and the like), cancers, pathologies linked to coagulation disorders and to dyslipoproteinaemias, pathologies linked to viral infections (hepatitis, AIDS and the like), or in the agronomic and veterinary fields and the like.

The present invention will be more fully described with the aid of the following examples which should be considered as illustrative and non-limiting. dr

LEGEND TO THE FIGURES

Table 1: Origin of the sequences used for the construction of the episome

FIG. 1: Diagram for the construction of the episome.

Figure 2:
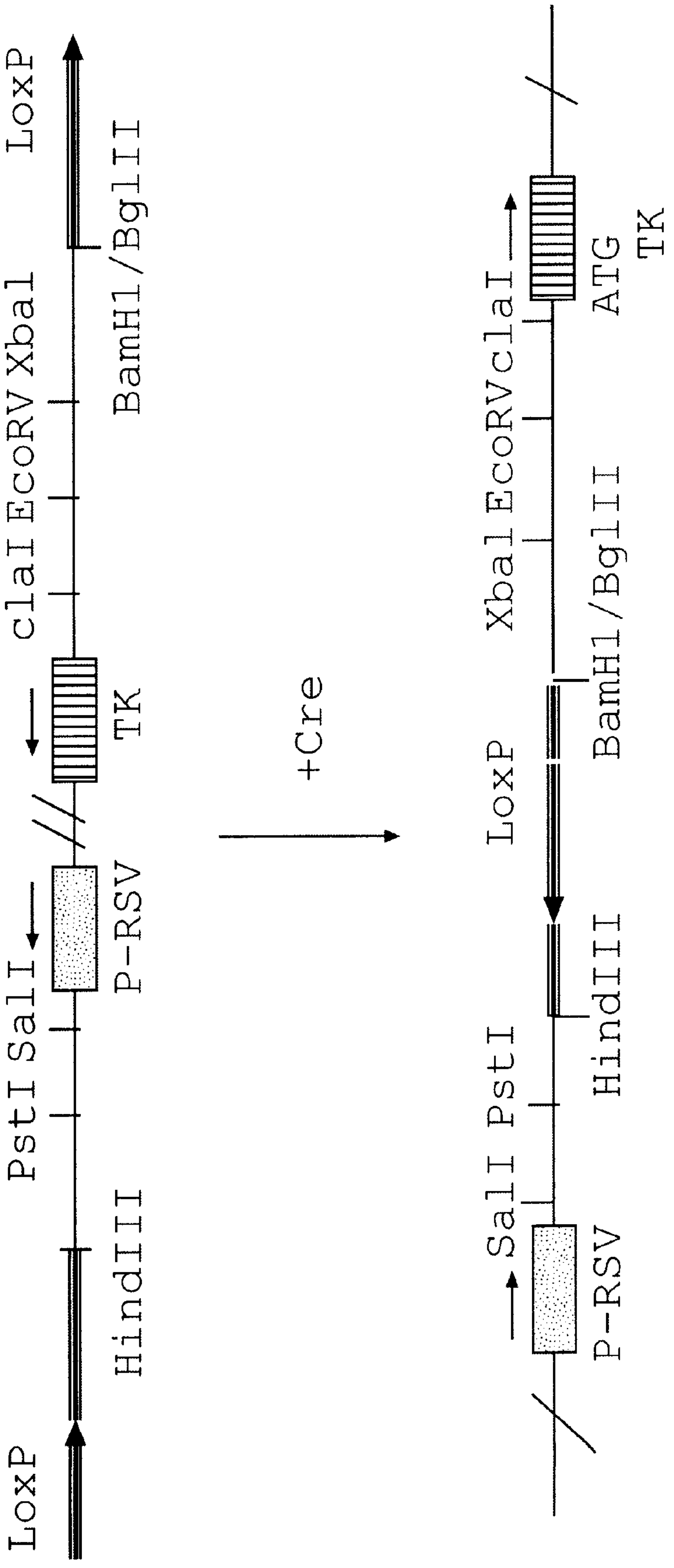

FIG. 2: Representation of the structure of the episome.

FIG. 3: Sequence between the promoter (P-RSV) and the expression cassette (TK-CITE-EBNA1) in the plasmid pLoXP-ori-TK-EBNA1 (A) and in the episome after ecombination (B, C and D)-SEQ ID No. 3.

Figure 4A:
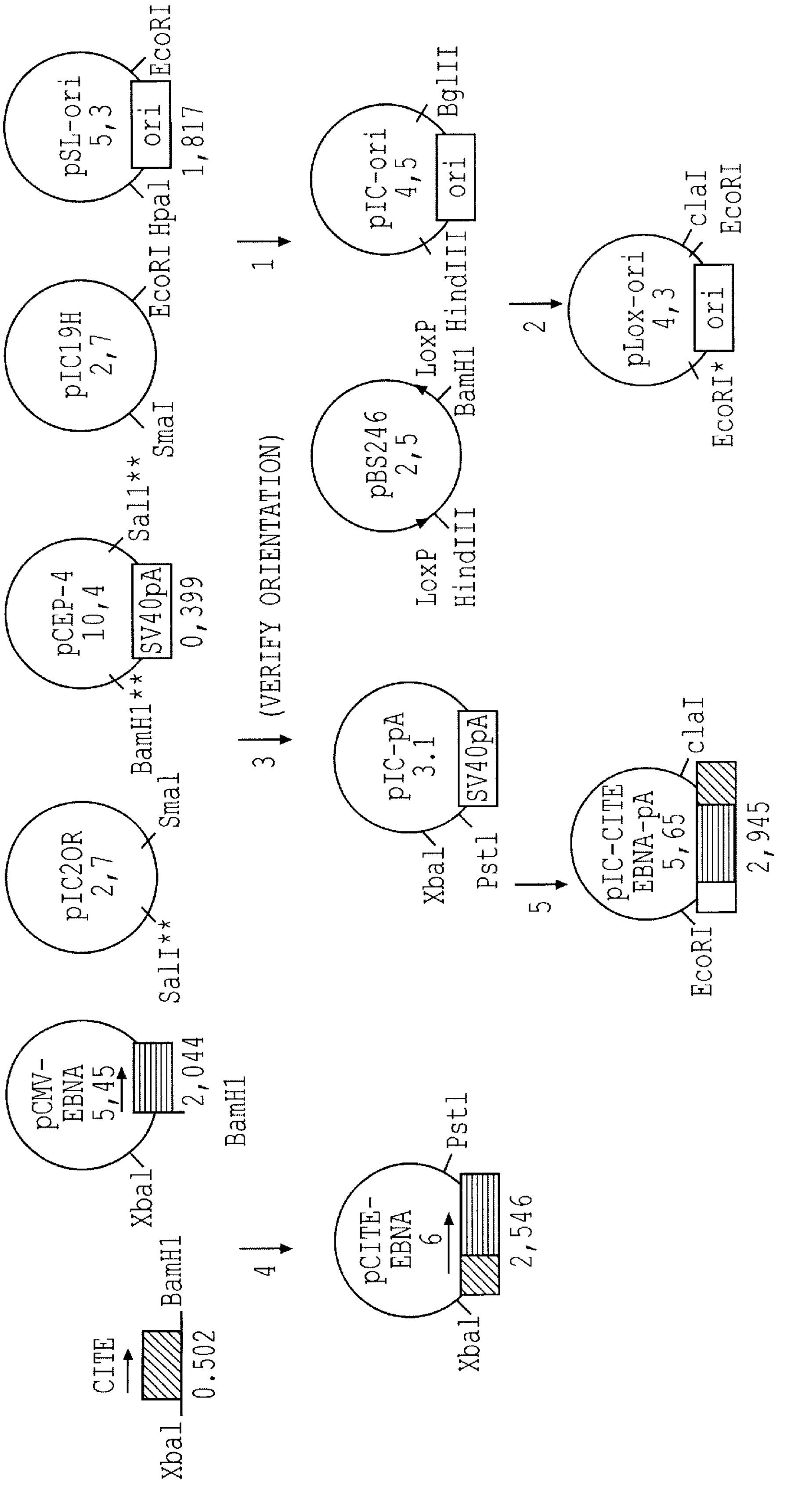
Figure 4B:
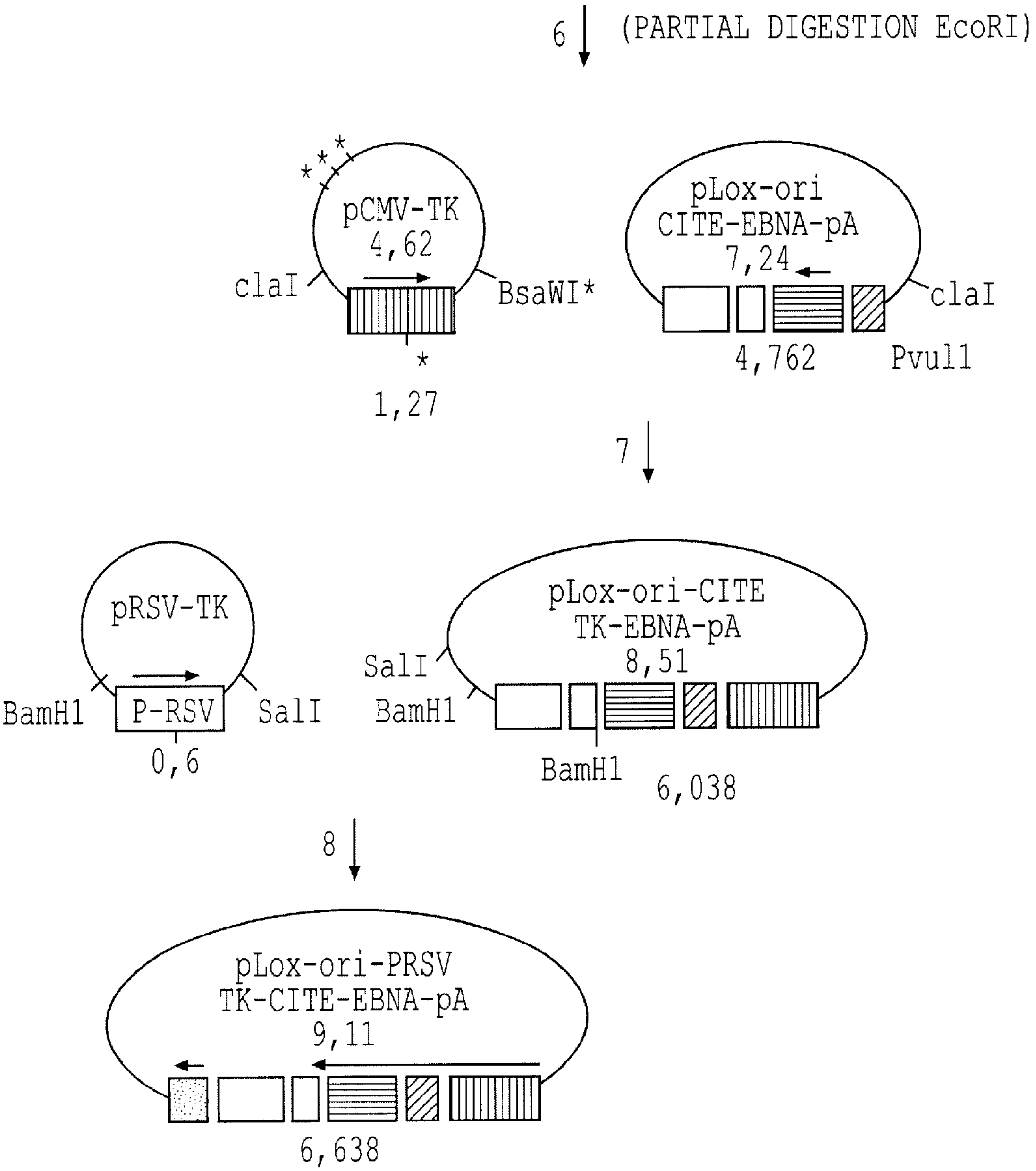

FIGS. 4*a*, 4*b*: Diagram of the stages of the loning of the cassette LoxP-ori-TK-EBNA1.

Figure 5:
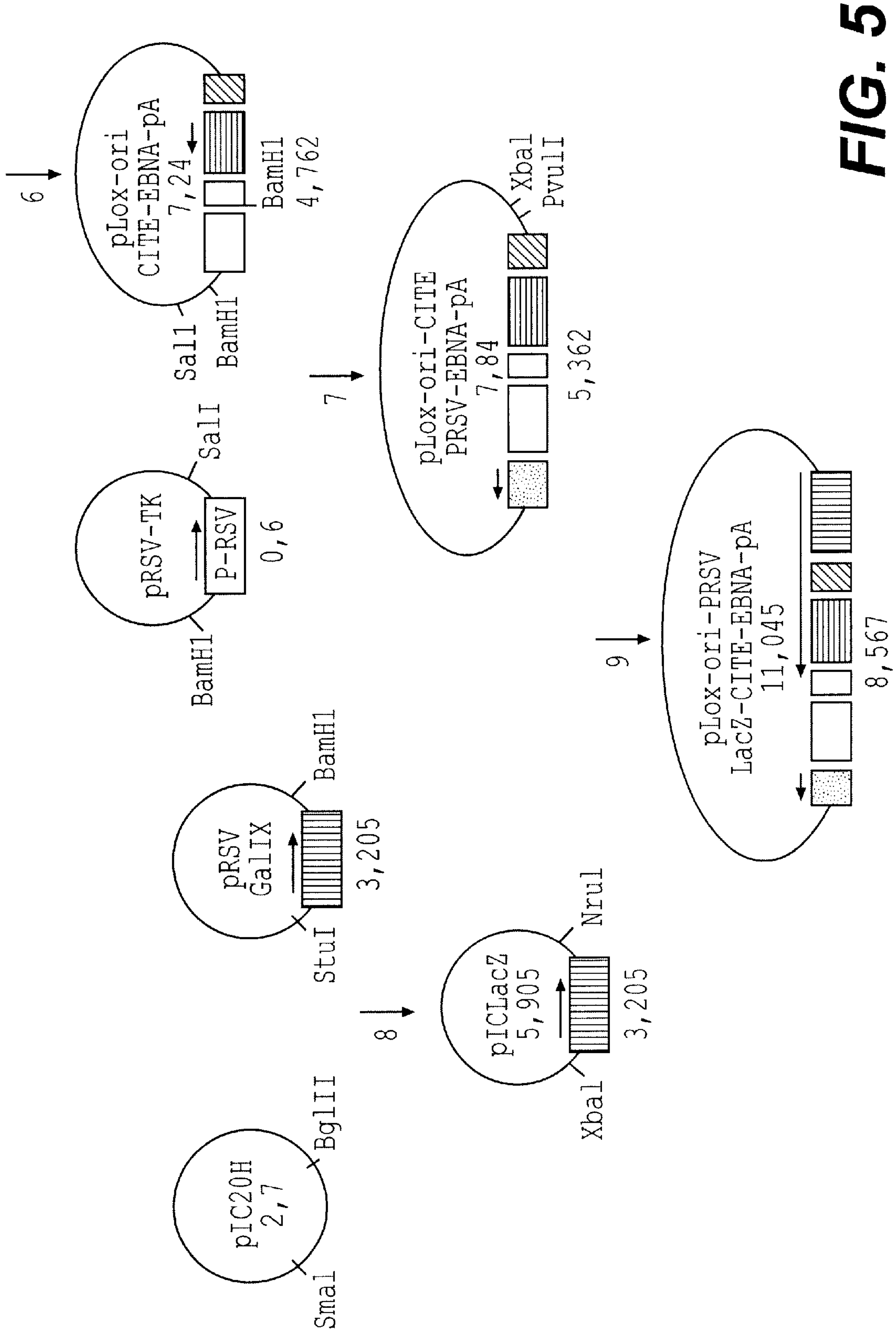

FIG. 5: Diagram of the stages of the cloning of the cassette LoxP-ori-LacZ-EBNA1.

FIG. 6: Representation of an adenoviral vector carrying a replicon and a regulated Cre expression cassette: $CRE_R$: regulated Cre, either at the level of the promoter, or by a fusion, or both. In (b), the orientation of the replicon makes it possible to place the cassette $CRE_R$ under the control of the promoter present in the replicon. The grey box corresponds to the LoxP sites.

FIG. 7: Representation of an adenoviral vector carrying a replicon and a regulated Cre expression cassette, the viral encapsidation region Psi (ψ) being included in the replicon. The grey box corresponds to the LoxP sites.

GENERAL CLONING AND MOLECULAR BIOLOGY TECHNIQUES

The conventional molecular biology methods, such as centrifugation of plasmid DNA in a caesium chloride-ethidium bromide gradient, digestions with restriction enzymes, gel electrophoresis, electroelution of DNA fragments from agarose gels, transformation into *E. Coli*, precipitation of nucleic acids and the like, are described in the literature (Maniatis et al., 1989, Ausubel et al., 1987). The nucleotide sequences were determined by the chain termination method following the procedure already presented (Ausubel et al., 1987).

The restriction enzymes were provided by New-England Biolabs (Biolabs), Bethesda Research Laboratories (BRL) or Amersham Ltd (Amersham).

For the ligations, the DNA fragments are separated according to their size on 0.7% agarose or 8% acrylamide gels, purified by electrophoresis and then electroelution, extracted with phenol, precipitated with ethanol and then incubated in a 50 mM Tris-HCl buffer pH 7.4 containing 10 MM $MgCl_2$, 10 mM DTT, 2 mM ATP, in the presence of T4 phage DNA ligase (Biolabs). The oligonucleotides are synthesized using the chemistry of the phosphoramidites protected in b by a cyanoethyl group (Sinha et al., 1984, Giles 1985) with the Biosearch 8600 automatic DNA synthesizer using the manufacturer's recommendations.

The plasmid DNAs are purified according to the alkaline lysis technique (Maniatis et al., 1989).

EXAMPLES

Example 1

Description of a vector in accordance with the invention (FIGS. 1–3)

FIG. 1 describes the general structure of a vector according to the invention and, more particularly, the region between the sequences allowing site-specific recombination. A more detailed construct is given in FIG. 2.

The orientation of the promoter (P) and of the cassette for expressing the transgene (TG) and the EBNA1 protein is indicated by arrows and therefore allows the expression of these two genes only after recombination in the presence of the recombinase Cre. The detail of the sequences between the promoter (P) and the gene after recombination is presented in FIG. 3. In this figure, the promoter is the RSV virus LTR (P-RSV) and the gene is the thymidine kinase TK gene. The first ATG of the messenger RNA, corresponding to that of the TK gene, is underlined. As illustrated in FIG. 1, the expression of EBNA-1 is obtained from a polycistronic messenger by internal initiation of the translation using the IRES (Internal Ribosome Entry Site) sequence also called CITE ("Cap Independent Translation Entry") sequence of the encephalomyocarditis virus (ECMV). The signal sequence for termination of transcription and for polyadenylation of the SV40 virus (pA) was introduced at the 3' end of the coding sequence of EBNA1. The oriP sequence is placed between the expression cassette TK-EBNA-1 and the RSV promoter. This sequence is active for replication only in the presence of EBNA-1; consequently, it functions only after recombination and formation of the episome.

Example 2

Construction of the plasmids LoxP-oriP-TK-EBNA1 and LoxP-ori-LacZ-EBNA1

The stages of the construction of the plasmids are presented in FIGS. 4 and 5 and the origin of the sequences used is summarized in Table 1.

2.1. Construction of the Plasmid pLoxP-oriP-TK-EBNA1 (FIG. 4)

1. The plasmid pSLori was digested with the restriction enzymes HpaI and EcoRI and the 1817 bp fragment obtained, corresponding to the orip sequence, was cloned between the SmaI and EcoRI sites of the plasmid pIC19H previously dephosphorylated, to give the plasmid pIC-ori (FIG. 4A).

2. The plasmid pIC-ori was digested at the HindIII and BglII sites, dephosphorylated and the 1900 bp fragment obtained was cloned between the HindIII (174) and BamHI (208) sites of the vector pBS246 to give the vector pLox-ori (FIG. 4A).

3. The 399 bp BamHI-SalI fragment of the vector pCEP4, corresponding to the sequence of the signal for the termination of transcription and of polyadenylation of the SV40 virus, was repaired with the Klenow DNA polymerase and then cloned between the SmaI and SalI sites (repaired with the Klenow DNA polymerase) of the vector pIC20R previously dephosphorylated, to give the vector pICpA (FIG. 4A).

4. The ECMV IRES sequence between nucleotides 16 and 518 of the vector pCITE-2 was amplified by PCR with the aid of the synthetic oligonucleotides 1 5'-GGCC TCTAGACAGCTGGTTATTTTCC-3' (SEQ ID No. 1) and 2 5'-GGCCGGATCCCATATTATCATCG-3' (SEQ ID No. 2) comprising the XbaI and PvuII (oligo 1) and BamHI (oligo 2) sites at their-5' end. The product obtained was digested with the restriction enzymes XbaI and BamHI and cloned between the XbaI and PstI sites of the vector pCMV-EBNA1 previously dephosphorylated, to give the vector pCITE-EBNA1. The sequence between ATG 12 of IRES, corresponding to the codon for initiation of translation, and the serine codon following the methionine codon of the EBNA1 protein, was deleted by site-directed mutagenesis with the aid of the PCR technique (ex-PCR site). The complete sequence of the IRES and of EBNA1 obtained after PCR was completely sequenced (FIG. 4A).

5. The XbaI-PstI fragment of the vector pCITE-EBNA1 (2546 bp) was cloned between the XbaI and PstI sites of the plasmid pICpA previously dephosphorylated, to give the vector pCITE-EBNA1-pA (FIG. 4A).

6. The ClaI-EcoRI fragment of the vector pCITE-EBNA1-pA (2945 bp) was cloned into the vector pLox-ori, partially digested at the EcoRI site situated at the end of ori, and then digested with ClaI and dephosphorylated to give the vector pLox-ori-CITE-EBNA1-pA (FIG. 4B).

7. The ClaI-BsaWl fragment (1270 bp) of the vector pCMV-TK, obtained by partial digestion with BsaW1 and repair of the BsaW1 site with the Klenow DNA polymerase, was cloned between the ClaI and PvuII sites of the vector pLox-ori-CITE-EBNA1-pA to give the vector pLox-ori-CITE-TK-EBRA1-pA (FIG. 4B).

8. The BamHI-SalI fragment (600 bp) of the plasmid pRSV-TK, corresponding to the sequence of the RSV LTR promoter, was cloned between the BamHI and SalI sites of the vector pLox-ori-CITE-TK-EBNA1-pA, previously dephosphorylated, to give the plasmid pLox-ori-pRSV-TK-CITE-EBNA1-pA (FIG. 4B).

2.2. Construction of the plasmid pLoxP-oriP-LacZ-EBNA1 (FIG. 5)

The clonings 1–6 described in Example 2.1 above and illustrated in FIG. 4A are common to the construction of the vectors pLox-ori-pRSV-TK-CITE-EBNA1-pA and pLox-ori-pRSV-LacZ-CITE-EBNA1-pA.

7. The cloning of the RSV LTR promoter was carried out according to step 7 of Example 2.1. (FIG. 5).

8. The BamHI-StuI fragment (3205 bp) of the vector pRSV-GalIX, corresponding to the LacZ gene preceded by a nuclear localization signal (NLS), was cloned between the SmaI and BglII sites of the vector pIC20H, previously dephosphorylated, to give the plasmid pICLacZ (FIG. 5).

9. The XbaI-NruI fragment (3205 bp) of the vector pICLacZ was cloned between the XbaI and PvuII sites of the vector pLox-ori-pRSV-CITE-EBNA1-pA to give the vector pLox-ori-pRSV-LacZ-CITE-EBNA1-pA (FIG. 5).

Example 3

Validation of the system by cotransfection of human cells (Hela-EBNA1; 143B-TK-) with the aid of the plasmids CMV-Cre (pBS185) and LoxP-oriP-TK-ERBN.1 or LoxP-oriP-LacZ-BBNA1.

3.1. Validation in Vitro

A Hela cell line stably expressing the EBNA1 gene was transfected with the plasmids pLoxP-oriP-LacZ-EBNA1 and a plasmid expressing the gene for the recombinase Cre under the control of the cytomegalovirus promoter (pBS185). The recombination efficiency and the functionality of the cassette for expressing the LacZ gene were evaluated by the β-galactosidase activity in the cells, observed only in the presence of the recombinase Cre. The results obtained demonstrate the efficiency of generation of the replicon under the action of the recombinase Cre, revealed by the activation of the expression of the LacZ gene after recombination between the LoxP sites and formation of the episome. Furthermore, after 3 weeks of culture of the cotransfected cells [passage once per week (1:10 dilution)], a maintenance of the proportion of cells expressing the LacZ gene is observed, whereas the expression of LacZ disappeared in the cells transfected with the control plasmid not possessing the replication origin orip, demonstrating the functional character of orip in the construct.

Likewise, a $TK^-$ cell line ($143TK^-$) is cotransfected with the plasmids LoxP-ori-TK-EBNA1 and pBS185. The transfected cells expressing the TK gene are selected in a HAT medium. The stability of expression of the TK gene during the cell divisions and therefore the activity of the oriP-EBNA1 system is verified by immunofluorescence with the aid of a monoclonal antibody specific for the TK protein of the herpes virus. The presence of the episome and its replication during cell divisions is revealed by the Hirt technique, followed by amplification of the episomal DNA by the PCR technique, with the aid of specific primers.

3.2. Validation in Vivo

The activity of these constructs in vivo is tested by intratumour injection (electroporation) of DNA of the plasmids pLoxP-ori-TK-EBNA1 or pLox-ori-LacZ-EBNA1 and pBS185 into tumours induced by subcutaneous injection of Hela or Hela-EBNA1 cells into nude mice. The injection of cells previously cotransfected with these same plasmids is performed in parallel. The maintenance of the transgene (TK or LacZ) in the tumours transduced by these constructs is analysed by immunohistochemistry, in comparison with a control plasmid not possessing the replication origin.

Example 4

Analysis of the system of recombination and of episomal maintenance 4.1-Construction of the plasmid pCre The plasmid p-Cre contains the gene for the recombinase Cre, fused in 5' with the nuclear localization signal of the SV40 virus T antigen and expressed using the thymidine kinase (TK) promoter of the herpes virus. A similar construct is prepared carrying, in place of the TK promoter, a promoter regulated by tetracycline or the MMTV promoter. Moreover, a cassette carrying a Cre-ER fusion is also prepared.

4.2-Construction of the Plasmid pRep

The replicon plasmid (pRep) containing a fusion of the phleomycin resistance gene with the β-galactosidase gene (Zeo LacZ), oriP and the cytomegalovirus early major promoter (P.CMV), without the EBNA1 protein, was constructed as follows.

The StuI-ClaI fragment (1149–4553) of the plasmid pRSV-Gal-IX containing the LacZ gene and the SV40 virus polyadenylation signal was cloned between the ClaI and EcoRV sites (2029–2032) of pLox-ori (Example 2 and FIG. 4) to give the plasmid pLox-ori-LacZ.

The BglII-BglII fragment (473–1226) of pCEP4 containing the CMV early promoter was cloned at the BamHI site of pLox-ori-LacZ to give pLX2.

The 5' end of the LacZ gene in pLX2 (XbaI-ClaI fragment) was substituted by the NcoI-ClaI fragment of the plasmid pUT651 (CAYLA, Table 1). To facilitate the cloning, this fragment was previously subcloned between the EcoRV and ClaI sites of the plasmid pIC2ORpA and then digested with XbaI and ClaI and cloned between the XbaI and ClaI sites of pLX2.

The control plasmid contains the same structure as pRep lacking the replication origin (OriP).

4.3-Construction of the Plasmid pRen-EBNA1

The cassette allowing the expression of EBNA1 from the ECMV IRES was constructed by site-directed mutagenesis from the plasmid pCITE-EBNA1-pA and cloned into the adenovirus shuttle vector pAdLX2 (5-2-2) to give pAdLX2-EBNA1 or pRep-EBNA1. The IRES as well as the beginning of EBNA1 were completely sequenced. The expression of EBNA1 using the IRES was analysed by Western blotting in Hela cells transfected with pRep-EBNA1. The plasmid pCMV-EBNA1 which served for the construction of pCITE-EBNA1pA serves as control.

4.4-Validation in Vitro 4.4.1-Analysis of the recombination and of the episomal maintenance in the Hela-EBNA1 cells In a first stage, experiments of transfection of Hela cells expressing the EBNA1 protein constitutively (Hela-EBNA1) with pRep alone or with pCre showed that the cotransfection of the two plasmids allowed the excision of the replicon and the induction of the expression of the β-galactosidase gene. The control cells transfected with the replicon plasmid alone show a constant but practically negligible β-galactosidase activity background noise. The expression of the transgene was monitored during successive passages of the cells, at the rate of 2 subcultures per week for-one month, which is equivalent to 24 cell divisions. In the cells transfected with pRep+pCre, the expression of β-galactosidase is maintained for the entire duration of the experiment whereas it was rapidly lost (after a few cell divisions) in the cells cotransfected with the control plasmid not carrying the replication origin oriP.

In a second stage, the cells cotransfected with (pRep+pCre) were selected in the presence of phleomycin. The episomal DNA was isolated by the Hirt technique, linearized or otherwise by digestion at the level of the unique XhoI site and then optionally digested with MboI in order to demonstrate that the DNA has indeed replicated in the eukaryotic cells. Southern blot analysis of the samples thus obtained made it possible to reveal the presence of a replicon of the expected size. The estimation of the number of copies per cell is from 1 to 10. The cells selected were then maintained in the presence or in the absence of a selection pressure. Under these two conditions, a similar maintenance of the expression of β-galactosidase with a slow and constant decrease during the cell divisions is observed. After 27 divisions, a β-galactosidase activity is still detectable in 25% of the cells by direct staining in vitro. These results correspond to a 97% segregational stability of the episome per division. They are in agreement with the published results; indeed, a rate of loss of 1 to 5% per division has been reported (Simpson et al., 1996).

4.4.2-Analysis of the functionality of EBNA1 in the Hela cells

Experiments of cotransfection of Hela cells with pRep-EBNA1 and pcre make it possible to check that EBNA1 is correctly expressed using IRES and ensures the maintenance of the expression of β-galactosidase during successive passages. The Hela-EBNA1 cells transfected with the same plasmids serve as control.

4.5. Validation in Vivo in a Model of a Tumour Induced in Nude Mice.

The Hela and Hela-EBNA1 cells are tumorigenic in nude mice, the subcutaneous injection of $10^6$ cells induces the formation of a tumour detectable in 8 days which grows very rapidly, and may be monitored for one month. In a first experiment, the Hela-EBNA1 cells transfected with pRep and pCre and then selected in vitro in the presence of phleomycin were injected. Analysis of the tumours (3 cm in diameter) at 21 days, after staining with X-gal demonstrates the maintenance of the replicon in vivo in this model.

In a second experiment, the Hela-EBNA1 cells transfected with pRep and then infected with AdCre (cf Example 5.2) were injected. Cells transfected with two plasmids derived from pRep allowing the expression of LacZ in the absence of recombination and carrying orip or otherwise, injected simultaneously, serve as control. The analysis of the tumours at 21 days demonstrates that the third generation Cre adenovirus allows the excision of the replicon and that its presence does not alter either the cell viability or the first stages of the establishment of the episome. It should be noted that no β-galactosidase activity was detectable in the cells transfected with the control plasmid not carrying orip. These results clearly show that the constructs according to the invention are functional in vivo in tumour cells; the episomes are also found to be stable after 21 days.

Example 5

Construction of 1st generation and 3rd generation recombined adenoviruses.

This example describes the construction of viral vectors according to the invention comprising a region which can generate, by site-specific recombination, a circular and replicative molecule in vivo. These viral vectors comprise in addition a sequence encoding the recombinase allowing the recombination.

5.1. Preparation of 1st Generation Adenoviruses (from the plasmids pBS185, pLoxP-oriP-TK-EBNA1 and pLoxP-oriP-LacZ-EBNA1).

The cassette for expressing the recombinase Cre and the complete sequence of the replicon including the LoxP sites are cloned from the vectors pBS185 and pLox-oriP-TK-EBNA1 or pLoxP-oriP-LacZ-EBNA1 into the E1 region of adenoviral vectors comprising a deletion of all or part of the E1 region (Addl327; ΔE1–ΔE3). The recombinant adenoviruses are isolated by conventional techniques of homologous recombination in the cells 293. The viral vectors may also be prepared by double recombination in *E. coli* with the aid of plasmids containing the genome of Adeno 5 ΔE1ΔE3, the viral genome then being encapsulated in an adenoviral particle in an appropriate line. For considerations of cloning capacity, the LacZ gene is advantageously replaced by a smaller marker gene.

5.2. Preparation of a 3rd Generation Adenovirus

The use of 3rd generation adenoviruses has certain advantages compared with those of the 1st generation, not only from the point of view of safety but also of a decrease in the inflammatory response and an increase in the stability of expression of the transgene. These vectors have, in addition, an increased cloning capacity and an absence of direct cytopathic effect in vitro and in vivo.

The 3rd generation vectors (Adl1007; ΔE1ΔE3ΔE4) may also be prepared by conventional techniques of homologous recombination in appropriate packaging cells (WO 96/22378) or by double recombination in *E. coli* followed by packaging.

The two adenoviruses were constructed by double recombination with the aid of *E. coli* cells containing a 3rd generation adenovirus genome pXL2811 (pRSV-bGal-ΔE1, ΔE3,ΔE4-dl1007-SspI) and pXL2789 (pΔE1,ΔE3,ΔE4-dl1007-SspI), and suicide plasmids (Kana-SacB) pMA37 or pXL3048, intended to modify the E1 region according to the strategy described above (Crouzet et al., 1997 PNAS, 94:1414; WO96/25506).

5.2.1. Preparation of Cre adenovirus (Cre-Ad)

The XhoI-BamHI fragment (451–2057) of the plasmid pMC-Cre (Table 1) was repaired with Klenow and cloned at the EcoRV site of the suicide plasmid pMA37.

The adenovirus genome obtained by double recombination with the plasmid pXL2811 was linearized by digestion with PacI and transfected into the IGRP2 cells (WO96/22378) with the aid of Lipofectamine (GIBCO). The 3.0 Cre-Ad thus produced was amplified in the same cells and then purified according to conventional techniques (caesium chloride) or by chromatography (FR96/08164).

The structure of the Cre adenovirus genome was confirmed by enzymatic digestion.

5.2.2. Preparation of Rep adenovirus (Rep-Ad)

The plasmid pLX2 was digested with BamHI and then recircularized in order to eliminate the SV40 polyadenylation signal, in 5' of the LacZ gene. The NotI-NotI fragment (1–6145) of the plasmid thus obtained was repaired by Klenow and then cloned at the EcoRV site of the suicide vector pXL3048 previously digested with BamHI and SalI, repaired by Klenow and then recircularized in order to destroy these two sites, to give the plasmid pAdLX2. The XhoI-SalI fragment-(441–3457) of the mutagenized plasmid PCITE-EBNA1pA was cloned at the XhoI site of the plasmid pAdLX2 previously obtained, to give the plasmid pAdLX2-EBNA1 (pRep-EBNA1).

Rep-Ad was obtained by recombination with the plasmids pAdLX2-EBNA1 and pXL2789, according to the techniques described above for Cre-Ad.

5.2.3. Preparation of Rep/Cre adenovirus (FIG. 6)

The Rep-Cre adenovirus carrying both the replicon and the gene for the recombinase Cre is constructed. This strategy makes it possible to increase the efficiency of transfer of the replicon and most particularly in vivo. The cassette for expressing Cre is inserted into the adenovirus genome in the E1, E3 or E4 regions. A perfectly regulated expression of the recombinase is sought in order to prevent the excision of the replicon from the adenovirus genome, during its propagation in the IGRP2 cells.

The regulation of the expression of the recombinase at the transcriptional level (tissue-specific promoter activated in vivo or inducible promoter) or. at the post-transcriptional level (Cre fusion with the domain of attachment of the steroid hormone receptor Cre-ER) was envisaged.

To construct these adenoviruses, the replicon is introduced into the plasmid pXL2789 as described in the preceding example. The cassette for expression of Cre comprising the promoter tet or MMTV, or a Cre-ER fusion is then introduced by double homologous recombination in *E. coli* in the said plasmid to generate the plasmids pRep-Cre1 (Rep and Cre in E1) and pRep-Cre2 (Rep in E1 and Cre in E4). These plasmids are then treated with PacI to extract the recombinant viral genome which is introduced into the IGRP2 cells to produce the corresponding viruses.

5.2.4. Preparation of ReD/Psi adenovirus (FIG. 7)

This construct makes it possible advantageously to avoid the contamination of the Rep-Cre-Ad with the adenovirus deleted of the replicon in the case where a perfect regulation of the activity of Cre may not be obtained. The strategy is based on the insertion of the encapsidation signal Psi into the replicon. The vector pXL3048 is modified by site-directed mutagenesis at the level of the ITR region in order to delete the encapsidation signal and to introduce a LoxP site, to give the plasmid pXL3048-ΔPsi-LoxP. The sequence of the replicon deleted of the "left LoxP" site is isolated by enzymatic digestion from the plasmids pAdLX2 or pAdLX2-EBNA1 and cloned at the EcoRV site of the plasmid pXL3048-APsi-LoxP.

Example 6

Validation of the system by co-infection with the two recombined adenoviruses:

The functionality of the viral vectors of the invention is controlled in vitro and in vivo:

6.1. Validation in Vitro, by Infection of Various Cell Lines.

The recombinase activity of the Cre adenovirus was demonstrated in vitro in Hela-EBNA1 cells transfected with pRep as well as in a mouse embryonic cell line (LoxP-βgal) in which the expression of LacZ may be activated by recombination between two LoxP sites.

The efficiency of the excision of the replicon from the adenoviral genome was studied in the IGRP2 cells co-infected with Rep-Ad and. Cre-Ad.

Direct analysis of the viral DNA isolated by the Hirt technique and digested with XhoI reveals a complete disappearance of the fragment corresponding to the replicon not excised from the genome of Rep-Ad, demonstrating the efficiency of the recombination between the two LoxP sites. Southern analysis of the same samples made it possible to reveal a 9.2 kb fragment corresponding to the replicon.

In the Hela cells co-infected with Rep-Ad and Cre-Ad, a β-galactosidase activity is observed at 48 h in 50% of the cells whereas no β-galactosidase activity is detectable in the cells infected with Rep-adeno alone. At 96 h, the number of cells expressing LacZ increases with cell division. After passage of the cells, the expression of LacZ is further maintained for at least 20 days after co-infection. These results demonstrate that (i) the replicon may be delivered efficiently into the cell by co-infection with these two adenoviruses, that (ii) the recombination releases the replicon and activates the expression of the transgene and that (iii) the replicon makes it possible to ensure the stable expression of the transgene during cell divisions.

6.2. Validation in Vivo

The validation in vivo was demonstrated by the transfer of normal human cells (keratinocytes, haematopoietic stem cells (CD34+), bronchial epithelial stem cells, myoblasts and the like) or cancerous human cells (MDA, HT29 and the like) previously co-infected with Rep-Ad and Cre-Ad, in nude mice.

The expression of the transgene and the stability of the episome during cell divisions are verified by the techniques described above.

TABLE 1

Origin of the sequences used for the construction of the episome

| Sequence | Fragment | Size (bp) | Origin |
|---|---|---|---|
| LoxP | NotI (1–296) | 34 | pBS246 (GIBCO-BRL) |
| RSV LTR | BamHI-SalI (478–1080) | 602 | pRSV-TK (WO95/14101) |
| oriP | EcoRI-HpaI (5052–3235) | 1817 | pSLori (WO95/14101) |
| SV40 polyA | BamHI-SalI (406–7) | 399 | pCEP-4 (In Vitrogen) |
| EBNA-1 | BamHI-PstI (759–2803) | 2044 | pCMV-EBNA (Clontech) |
| IRES | (16–518) | 502 | pCITE 2a (Novagen) |
| TK | ClaI-BsawI (1721–556) | 1165 | pCMV-TK-E1 Gene Therapy 3 (1996) 315) |
| pIC19H | | 2700 | Marsh et al., |
| PIC20H | | 2700 | Gene 32 (1984) |
| pIC20R | | 2700 | 481 |
| pBluescriptII-KS | | 2850 | (Stratagene) |
| hCMV | BglII-BglII (473–1226) | 753 | pCEP4 (IN VITROGEN) |
| LacZ | StuI-BamH1 (1149–4354) | 3205 | pRSVGalIX (L. Stratford-Perricaudet, J. Clin. Invest 1992 p 626) |
| hCMV-Cre-MTpA | HindIII-HindIII (0–3400) | 3400 | pBS185 (GIBCO-BRL) |
| Zeo-Lac | NcoI-ClaI (750–1980) | 1230 | pUT641 (CAYLA) |

What is claimed is:

1. A replication defective adenovirus comprising:

(1) a DNA region comprising:

(a) an oriP replication origin of an Epstein-Barr virus (EBV);

(b) a gene of interest;

(c) a promoter functional in mammalian cells;

(d) a nucleic acid sequence encoding an EBNA1 protein; and (e) an Internal Ribosome Entry Site (IRES) sequence of an encephalomyocarditis virus (EMCV)

wherein the IRES sequences is located between the gene of interest and the nucleic acid sequence encoding the EBNA1 protein; and (2) two recombination nucleic acid sequences that are capable of undergoing site-specific recombination with each other and positioned in direct orientation, wherein the DNA region is located between the two recombination nucleic acid sequences such that upon site-specific recombination of the recombination nucleic acid sequences, the nucleic acid sequence encoding the EBNA1 protein and the gene of interest are operatively associated with the promoter.

2. The replication defective adenovirus according to claim 1, wherein the two recombination nucleic acid sequences undergo site-specific recombination with each other in the presence of a recombinase.

3. The replication defective adenovirus vector of claim 2, wherein the two recombination nucleic acid sequences are derived from a bacteriophage.

4. The replication defective adenovirus vector of claim 3, wherein the bacteriophage is P1 bacteriophage.

5. The replication defective adenovirus vector of claim 4, wherein the two recombination nucleic acid sequences are the inverted repeat sequences of the loxP region of P1 bacteriophage.

6. The replication defective adenovirus vector of claim 2, further comprising a gene encoding recombinase, wherein said gene is not located within said DNA region.

7. The replication defective adenovirus vector of claim 6, wherein said gene encoding recombinase is under the control of an inducible promoter.

8. The replication defective adenovirus vector of claim 7, wherein the inducible promoter comprises the MMTV promoter which is inducible by dexamethasone, or a promoter inducible by tetracycline.

9. The replication defective adenovirus vector of claim 7, wherein said gene encoding the recombinase further comprises a regulatory element encoding the binding domain of a hormone receptor.

10. The replication defective adenovirus vector of claim 9, wherein the hormone receptor is selected from the group consisting of a glucocorticoid receptor, a mineralocorticoid receptor, a thyroid receptor, an oestrogen receptor, an aldosterone receptor, and a retinoic acid receptor.

11. The replication defective adenovirus vector of claim 1, wherein said DNA region further comprises a virus encapsidation region.

12. The replication defective adenovirus vector of claim 11, wherein the replication defective adenovirus vector lacks all or part of an E1 region.

13. The replication defective adenovirus vector of claim 12, wherein said replicaiton defective adenovirus vector lacks all or part of an E4 region.

14. An isolated cell comprising the replication defective adenovirus vector of claim 1.

15. The cell of claim 14, wherein the cell is a eukaryotic cell.

16. A composition comprising the replication defective adenovirus vector of claim 1 and a pharmaceutically acceptable carrier.

17. A process for preparation of circular replicative DNA molecules, comprising contacting a population of cells of claim 15 with a recombinase under conditions which permit in situ site-specific recombination of the two recombination nucleic acid sequences.

18. The process according to claim 17, wherein the contacting step comprises transfecting the cells with a vector comprising a DNA sequence operatively associated with a promoter, wherein the DNA sequence encodes recombinase.

19. A process for preparing replicative circular DNA molecules, comprising:

(i) transforming cells with the replication defective adenovirus vector of claim 7; and (ii) inducing expression of the recombinase.

20. The replication defective adenovirus of claim 10, wherein the hormone receptor is the glucocorticoid hormone receptor.

* * * * *

UNITED STATES PATENT AND TRADEMARK OFFICE

CERTIFICATE OF CORRECTION

PATENT NO. : 6,630,322 B1 
DATED : October 7, 2003
INVENTOR(S) : Michel Perricaudet et al.

It is certified that error appears in the above-identified patent and that said Letters Patent is hereby corrected as shown below:

Title page,
Item [76], Inventors, “Bis rue Lacépéde,” should read -- bis rue Lacépède, --; and “782280” should read -- 78280 --.
Insert Item after Inventors:
-- [73] Assignee: Gencell S.A., Vitry-sur-Seine (FR) --.

Column 21,
Line 52, “sequences is” should read -- sequence is --.

Signed and Sealed this

Twentieth Day of January, 2004

JON W. DUDAS
*Acting Director of the United States Patent and Trademark Office*